United States Patent [19]

Juchem

[11] Patent Number: 5,549,922
[45] Date of Patent: Aug. 27, 1996

US005549922A

[54] METHOD OF MAKING FLOUR-CONTAINING EDIBLE SEMIFINISHED PRODUCTS

[75] Inventor: Franz-Josef Juchem, Eppelborn, Germany

[73] Assignee: Juchem GmbH, Eppelborn, Germany

[21] Appl. No.: 794,583

[22] Filed: Nov. 19, 1991

Related U.S. Application Data

[63] Continuation-in-part of Ser. No. 773,778, Oct. 10, 1991, which is a continuation of Ser. No. 510,095, Apr. 17, 1990, abandoned.

[30] Foreign Application Priority Data

Apr. 24, 1989 [DE] Germany .................. 39 13 420
Nov. 26, 1990 [DE] Germany .................. 40 37 499

[51] Int. Cl.$^6$ ..................................................... A23L 3/00
[52] U.S. Cl. ..................... 426/618; 426/312; 426/320; 426/498
[58] Field of Search ............................. 426/618, 498, 426/312, 320

[56] References Cited

U.S. PATENT DOCUMENTS

| | | | |
|---|---|---|---|
| 1,017,361 | 2/1912 | Adam | 426/498 |
| 3,041,176 | 6/1962 | Baker | 426/498 |
| 3,332,371 | 7/1967 | Brastad | 426/498 |
| 3,928,646 | 12/1975 | Hartley | 426/498 |
| 3,970,763 | 7/1976 | Moran et al. | 426/498 |
| 4,364,961 | 12/1982 | Darley et al. | 426/498 |
| 4,568,550 | 2/1986 | Fulger et al. | 426/498 |

FOREIGN PATENT DOCUMENTS

| | | | |
|---|---|---|---|
| 0040887 | 5/1980 | European Pat. Off. | 422/39 |
| 3445990 | 12/1984 | Germany | 422/39 |

*Primary Examiner*—Anthony J. Weier
*Attorney, Agent, or Firm*—Henry M. Feiereisen

[57] ABSTRACT

The microorganism population of a flour-containing semifinished product (such as dough) is reduced by forming a suspension of flour with a liquid (particularly water, milk and/or the flowable ingredients of eggs), and subjecting the suspension to the action of an inert gas (such as carbon dioxide gas) for a period of between approximately 5 and 240 minutes at a pressure of between approximately 2 and 100 bars. The thus obtained semifinished product can be stored for extended periods of time in a standard refrigerator rather than only in a freezer. The method can further comprise the step or steps of stirring the suspension for the purposes of homogenization and/or abruptly reducing the pressure of gas upon elapse of the interval of 5–240 minutes and/or repeatedly varying the pressure of gas and/or adding to the suspension an animal and/or vegetable fat and/or adding to the suspension salt, sugar, an aromatic substance and/or another additive.

18 Claims, No Drawings

METHOD OF MAKING FLOUR-CONTAINING EDIBLE SEMIFINISHED PRODUCTS

CROSS-REFERENCE TO RELATED CASE

This is a continuation-in-part of patent application Ser. No. 07/773,778 filed Oct. 10, 1991 by Günter Lehmann and Franz-Josef Juchem for "Method of disinfecting and preserving an organic product" which is a continuation of Ser. No. 07/510,095 filed Apr. 17, 1990 and now abandoned.

BACKGROUND OF THE INVENTION

The invention relates to foodstuffs in general, and more particularly to improvements in methods of preparing semifinished edible products. Still more particularly, the invention relates to improvements in methods of preparing semifinished edible products which contain flour.

Changing eating habits of the populace compel the food industry to devise new modes of making, preserving and preparing various edible products, particularly semifinished products which are ready for consumption with a minimum of preparation, e.g., merely by cooking, boiling, broiling or grilling. Such edible products are in great demand by employees and other persons who have little time left for the preparation of meals. Many presently known and highly popular semifinished products can be stored for reasonably long periods of time in freezers but not in refrigerators or without refrigeration. This prevents a rather large segment of the population from purchasing and processing such types of semifinished products, namely all households which are not equipped with a freezer. Large quantities of semifinished edible products are also purchased and used by many food processing establishments including restaurants, delicatessens, mess halls and others. Storage of semifinished products in deep freezers contributes significantly to the cost of operation and hence to the price of meals. Thus, there exists an urgent need for semifinished edible products which can be stored in refrigerators (or even without refrigeration) for reasonable periods of time.

The above applies especially for many flour-containing semifinished edible products, such as bakery products, sauces, various types of dough and those containing the edible ingredients of eggs. The flour, such as finely ground wheat flour, invariably contains large counts of germs Therefore, those industries which deal with the preparation of flour-containing semifinished edible products attempt to reduce the bacterial count of such products or to sterilize them to thus render them capable of standing longer periods of storage. Heretofore known attempts to sterilize flour-containing foodstuffs include exposure to radioactive radiation. However, such treatment is not popular with the consumers and is an important reason that many consumers avoid the purchase of foodstuffs which were treated with radioactive rays.

The situation is aggravated if the flour is mixed with one or more liquids, such as water, milk and/or the flowable constituents or contents of eggs. These mixtures constitute ideal breeding grounds for numerous microorganisms which are contained in flour and/or in the liquid additives. The thus obtained semifinished products (e.g., various doughs) cannot be stored at room temperature, even for relatively short or very short periods of time, i.e., they must be stored in freezers or must be baked, fried, cooked and/or otherwise treated for immediate consumption. Heating in an oven or otherwise ensures destruction of microorganisms in the thus obtained finished edible substances.

OBJECTS OF THE INVENTION

An object of the invention is to provide a method of making semifinished flour-containing edible products which can be stored for extended periods of time in facilities other than freezers.

Another object of the invention is to provide a method which renders it possible to store mixtures of flour with liquids in regular refrigerators at temperatures well above those prevailing in a freezer.

A further object of the invention is to provide a method which renders it possible to store various doughs at temperatures well above those in a freezer.

An additional object of the invention is to provide a semifinished product which is obtained in accordance with the above outlined method.

A further object of the invention is to provide a novel and improved method of reducing the content of microorganisms of flour-containing edible substances.

Another object of the invention is to provide a novel and improved method of making flour- and liquid-containing semifinished edible products which can be safely stored in refrigerators.

SUMMARY OF THE INVENTION

The invention is embodied in a method of reducing the microorganism population of flour-containing semifinished products. The improved method comprises the steps of forming a suspension of flour and a liquid (such as water and/or milk and/or the flowable contents of eggs), and subjecting the suspension to the action of an inert gas (namely a gas which does not react with the constituents of the suspension) for an interval of between approximately 5 and 240 minutes. The subjecting step includes maintaining the gas at a pressure of between approximately 2 and 100 bars.

The subjecting step can further include repeatedly varying the pressure of the gas, and the method can further include the step of abruptly reducing the pressure of gas (particularly to atmospheric pressure) upon elapse of the aforementioned interval.

The method can further comprise the step of homogenizing the suspension, and such homogenizing step can include agitation (for example, stirring).

The method can also comprise the step of adding to the suspension an animal and/or a vegetable fat and/or the step of adding to the suspension one or more additives (such as sugar, salt and/or an aromatic substance).

The inert gas is preferably carbon dioxide gas; however, it is equally possible to utilize one or more other inert gases such as alkanes or alkenes containing up to three carbon atoms, nitrous oxide, sulfur hexafluoride, a noble gas, nitrogen, oxygen and air.

The novel features which are considered as characteristic of the invention are set forth in particular in the appended claims. The improved method itself, however, together with additional features and advantages thereof, will be best understood upon perusal of the following detailed description of certain presently preferred specific embodiments.

DESCRIPTION OF PREFERRED EMBODIMENTS

The improved method can be resorted to for the preparation of a variety of semifinished edible products which contain wheat flour and/or other types of flour. The method is suitable for batch type operation or for the continuous making of a flour-containing semifinished edible substance which is ready for storage in a freezer as well as in a refrigerator. All that is necessary is to employ a suitable receptacle wherein a metered quantity or a continuous or discontinuous flow or stream of flour in suspension with a liquid (such as water, milk and/or the flowable contents of eggs) is subjected to the action of an inert gas which is maintained above atmospheric pressure, particularly at a pressure of approximately 2 to 100 bars. The interval of treatment is normally between approximately 5 and 240 minutes, and such treatment can be carried out at or above or below room temperature. If the treatment involves sterilization or pasteurizing of successive batches of flour, the batches are admitted seriatim into a suitable vessel and are contacted with an effective amount of a selected liquid. The vessel is sealed and an inert gas (namely carbon dioxide gas or another gas which does not react with the ingredients or constituents of the suspension) is thereupon admitted into the vessel and is maintained at a desired pressure of normally not less than 2 bars and normally not more than 100 bars. The treatment is completed after the elapse of an interval of normally not less than five minutes and normally not more than 240 minutes. The thus obtained product contains reduced number of microorganisms or is even sterile.

The treatment can involve maintaining the interior of the sealed suspension-containing vessel at a constant pressure during the entire selected interval of time, or repeated raising and lowering of the pressure and/or the temperature. It is often advisable to terminate the treatment of a batch by abruptly lowering the pressure in the vessel to atmospheric pressure.

It is equally within the purview of the invention to homogenize the suspension in the vessel, either continuously or during certain stages of the interval of subjecting a batch to the pressure of an inert gaseous fluid, such as carbon dioxide gas. The homogenizing step can involve stirring the contents of the vessel and/or other modes of agitation.

Still further, the treatment can involve the addition of selected quantities of animal and/or vegetable fats which are or can be homogeneously distributed in the suspension while the suspension is being agitated and while the interior of the vessel which confines the suspension is maintained at a pressure of between approximately 2 and 100 bars. It is also possible to introduce into the suspension one or more additives, for example, sugar, salt and/or one or more aromatic substances to enhance the taste and/or flavor and/or appearance of the semifinished product.

Carbon dioxide gas is the presently preferred gaseous fluid because it is universally acceptable to authorities in charge of supervising the food preparing and processing industries, and also because it is available in large quantities at a reasonable cost and free of impurities. However, it is equally within the purview of the invention to employ any other physiologically acceptable inert gas, such as alkanes or alkenes containing not more than three carbon atoms, nitrous oxide, sulfur hexafluoride, a noble gas and/or nitrogen. In fact, and especially if the interior of the vessel is maintained at an elevated pressure, the suspension can be acted upon by oxygen and/or air. The above enumerated gases can be utilized singly or in any selected admixture to each other.

The procedure is analogous if the method involves the treatment of a continuous or discontinuous flow of a suspension of flour and one or more liquids. All that is necessary is to ensure that each unit length of the stream or flow is treated for a required interval of time and at an optimum pressure within the aforementioned range of pressures.

An important advantage of the improved method is its simplicity and the low cost of treatment of the suspension for storage in a freezer or in a refrigerator. It has been found that the improved method of treating a suspension with an inert gas invariably ensures a pronounced reduction of the microorganisms and the destruction of pathogenic microorganisms to thus avoid the risk of contamination of the semifinished product by the gas even if the product is stored in a refrigerator for an extended period of time.

Another important advantage of the improved method is that it does not affect the appearance and/or taste of the thus obtained storable semifinished product.

EXAMPLE

A dough for the making of crepes was prepared in the following way: Wheat flour was mixed with egg white, egg yolk and mineral water, and the thus obtained suspension was homogenized by stirring. Salt was added to the suspension during stirring, and the thus obtained product was thereupon sterilized at a temperature of 40° C. for a period of approximately 120 minutes at a pressure of 60 bars in an atmosphere of carbon dioxide gas. The pressure was abruptly reduced to atmospheric pressure upon elapse of the 120-minute interval. The thus obtained semifinished edible product was ready for storage in a sterile receptacle in the form of a ready-to-use dough, and it was found that the microorganism population was reduced to a level which rendered it possible to store the product not only in a freezer but also in a refrigerator. Thus, by the simple expedient of subjecting the suspension of flour, salt, mineral water and flowable ingredients of eggs to the pressure of an inert gas for a requisite interval of time, the thus obtained semifinished product was storable in a refrigerator in a state of readiness for the making of pancakes or other dishes.

The improved method can be resorted to with equal or similar advantage for the making of many other types of flour-containing semifinished products including bread dough, dough for the making of pasta or noodles, sauces and products which can be termed semifinished sauces. The liquid contents of the thus obtained semifinished products are or can be sufficiently high to permit immediate baking, cooking, frying or other treatment for conversion into ready-to-serve food products.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A method of reducing the microorganism population of flour-containing semifinished products, comprising the steps of:

forming a suspension of flour and a liquid;

subjecting the suspension to the action of an inert gas for an interval of between 5 and 240 minutes, including maintaining the gas at a pressure of between approximately 2 and 100 bars to produce a substantially sterilized semifinished product that is capable of being stored in a refrigerator until being used for further processing; and abruptly reducing the pressure of gas after elapse of said interval.

2. The method of claim 1, wherein the liquid is water.

3. The method of claim 1, wherein the liquid is a flowable ingredient of eggs.

4. The method of claim 1, wherein the liquid is milk.

5. The method of claim 1, wherein the liquid is a mixture of water and a flowable ingredient of eggs.

6. The method of claim 1, wherein the liquid is a mixture of water and milk.

7. The method of claim 1, wherein the liquid is a mixture of milk and a flowable ingredient of eggs.

8. The method of claim 1, wherein the liquid is a mixture of water, milk and a flowable ingredient of eggs.

9. The method of claim 1, wherein said subjecting step further includes repeatedly varying the pressure of gas.

10. The method of claim 1, wherein the inert gas is carbon dioxide.

11. The method of claim 1, further comprising the step of homogenizing the suspension.

12. The method of claim 10, wherein said homogenizing step includes stirring.

13. The method of claim 1, further comprising the step of adding animal and/or vegetable fat to the suspension.

14. The method of claim 1, further comprising the step of introducing into the suspension at least one additive.

15. The method of claim 14, wherein the at least one additive is sugar.

16. The method of claim 14, wherein the at least one additive is salt.

17. The method of claim 14, wherein the at least one additive is an aromatic substance.

18. The method of claim 1, further comprising the step of packaging a product containing said flour and said liquid in a semifinished condition, said packaging step being carried out after said subjecting step.

* * * * *